United States Patent
Katoh

(10) Patent No.: US 6,632,019 B2
(45) Date of Patent: Oct. 14, 2003

(54) RADIOGRAPHIC APPARATUS

(75) Inventor: Mikihiko Katoh, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 229 days.

(21) Appl. No.: 09/871,669

(22) Filed: Jun. 4, 2001

(65) Prior Publication Data

US 2002/0003864 A1 Jan. 10, 2002

(30) Foreign Application Priority Data

Jul. 7, 2000 (JP) ........................................ 2000-205972

(51) Int. Cl.[7] ................................................. H05G 1/02
(52) U.S. Cl. ........................................ 378/197; 378/196
(58) Field of Search ................................. 378/193, 196, 378/197, 190, 208

(56) References Cited

U.S. PATENT DOCUMENTS 5,751,788 A * 5/1998 Khutoryansky et al. .... 378/197
6,435,713 B1 * 8/2002 Iizuka ........................ 378/195

* cited by examiner

Primary Examiner—Louis Arana
(74) Attorney, Agent, or Firm—Kanesaka & Takeuchi

(57) ABSTRACT

In a radiographic apparatus, a pole to which an X-ray tube device is fixed is independently evacuated on a head side or a foot side of a top board through an operation of an X-ray tube pole evacuating switch. A subject or patient is laid on a top board, and a secondary X-ray tube device suspended from an overhead traveling portion is moved to be positioned over a concerned portion of the subject. Then, an X-ray image detecting portion moving switch is operated so that an X-ray image detecting portion is moved to a position, corresponding to the concerned portion under the top board. Under the state, remote radiographing, such as chest radiographing, is carried out. Thus, the remote radiographing can be carried out by a radiographic stand capable of fluoroscopying and radiographing without separately installing a radiographing device.

7 Claims, 7 Drawing Sheets

8 x-ray tube device

RADIOGRAPHIC APPARATUS

BACKGROUND OF THE INVENTION AND RELATED ART STATEMENT

The invention relates to a radiographic apparatus, more particularly, to a radiographic apparatus which can perform a remote radiographing for taking an image, such as chest area, in combination with a secondary overhead suspension type X-ray tube device.

There are clinics and hospitals equipped with a remote and proximity operating type fluoroscopic radiographing stand, a separately installed X-ray tube device which can carry out a chest radiographing and the like, a separately installed Lieder's radiographic stand, and a top board, installed in one X-ray examination room or a separate X-ray examination room.

The fluoroscopic radiographing stand is classified in various types suitable for an operational method and a clinical method. For example, there are an over-tube type fluoroscopic radiographing stand, and an under-tube type fluoroscopic radiographing stand according to the positions of the X-ray tube devices. In the over-tube type fluoroscopic stand, the X-ray tube device is disposed over a top board, and a spot radiographing device and an imaging system are located under the top board.

In the over-tube type fluoroscopic radiographing stand, since the X-ray tube device is disposed at a position away from the top board, a wide space can be used over the top board, so that a subject or patient can be observed easily and a physical position of the subject can be easily changed. Also, when the device is operated, since an operator of the device need not pay much attention to the subject, the operator can easily act to thereby obtain a good diagnostic efficiency. Also, since the space over the top board is large, in case various diagnoses, such as myelography and IVR, are made, or other diagnoses, such as endoscope diagnosis or ultrasonic wave diagnosis, are made with respect to the subject, the over-tube type fluoroscopic radiographing stand is advantageous. Also, the over-tube fluoroscopic radiographing stand has a structure facilitating to hold the spot radiographing device or the like under the top board. However, in view of a mechanical structure of the device, a distance from an X-ray tube focal point to an image receiving surface is limited to a range of 1.1 to 1.5 m.

Also, in order to take a radiograph of a skeleton system or the like, a radiographing mechanism capable of Bucky's radiographing by using a radiographic cassette is disposed on a back side of the top board, and a simple radiographing is carried out by a separately installed X-ray tube device.

Also, since the chest radiographing requires a distance between the focal point and a film for about 2 meters, it is impossible to carry out the chest radiographing by using the above fluoroscopic radiographing stand. Therefore, the chest radiographing is carried out by the separately installed X-ray tube device and separately installed Lieder's radiographic stand.

Also, when radiographing for a side surface of the subject is made in a process of an examination, the side portion of the subject must be laid on the top board. However, in case the subject can not be moved, there is a case wherein a side surface radiographing is carried out by a separately installed X-ray tube device and a radiographing device.

In order to effectively use the equipment, there is a case wherein the above-mentioned fluoroscopic radiographing stand, the X-ray tube device and the Lieder's radiographic stand for radiographing the chest or the like, and the top board are installed in one X-ray examination room to thereby carry out the X-ray examination based on a time-sharing.

FIG. 6 shows the over-tube type fluoroscopic radiographing stand. Normally, the X-ray tube device 8 mounted on the fluoroscopic radiographing stand and an image receiving system 9 facing the same to sandwich the top board 4 therebetween are interlocked to move parallel to the top board 4, and the fluoroscopic radiographing can be carried out through a vertical movement of the X-ray tube device 8. While the X-ray tube device 8 moves in the front and rear directions with respect to the image receiving system 9, in view of a mechanical structure of the device, the distance from a focal spot to the image receptor (hereinafter referred to as "FID"), i.e. a distance from a reference plane of an effective focal point of the X-ray tube device 8 to a crossing point where a reference axis crosses an image receptor surface of the image receiving system 9, is in the order of 1.1 to 1.5 m.

Therefore, in case a chest radiographing is carried out from a remote position, such as 2 to 3 m, as shown in FIG. 7, a secondary X-ray tube device 1a separately installed to a overhead traveling portion 7, and another device where a radiographing device 11 is attached to the Lieder's radiographic stand are used. At this time, FID is set in the order of 2.0 to 3.0 m.

Also, in an under-tube type fluoroscopic radiographing stand with a proximity operation type, the X-ray tube device is disposed on a back side of the top board, and the spot radiographing device and the imaging system are located in front of the top board. FID is in the order of 0.8 to 1.2 m. When the remote radiographing for the chest or the like is carried out, as shown in FIG. 8, the X-ray tube device 8 and the image receiving system 9 are evacuated toward a head or feet portion of the subject, and the secondary X-ray tube device 1a separately attached to the overhead traveling portion 7 is used in combination with a secondary radiographing device 11 disposed under the top board 4 to take the image. At this time, the radiographing device 11 located on the back side of the top board 4 of the fluoroscopic radiographing stand can be manually moved in the longitudinal direction of the top board 4, and has a grid for removing scattered rays. A cassette (not shown) having a radiographing film and an intensifying screen therein is disposed in the radiographing device Also, in either the over-tube type or the under-tube type fluoroscopic radiographing stand, when a side radiographing is carried out, as shown in FIG. 9, radiographing is carried out by using the separately installed secondary X-ray tube device 1a attached to the overhead traveling portion 7 and mounting an X-ray cassette 23 to the fluoroscopic radiographing stand.

In the conventional fluoroscopic radiographing stand structured as described above, the X-ray tube device 8, a pole for holding the same and the image receiving system 9 facing the X-ray tube device 8 to sandwich the top board 4 therebetween are interlocked to move parallel to the top board 4, and the X-ray tube device 8 is transferred in the front and rear directions with respect to the image receiving system 9. However, in view of a mechanical structure of the device, its FID is in a range of 1.1 to 1.5 m. Therefore, in case the remote radiographing for taking a radiograph for a chest or the like, where a magnification ratio is suppressed, i.e. FID is 2 to 3 m, is carried out, it is necessary to lengthen a distance between the X-ray tube device 8 and the image receiving system 9. However, in the conventional fluoroscopic radiographing stand, since the movable areas of the same are limited and further they are interlocked, only the X-ray tube device 8 can not be evacuated to a different position through a horizontal movement. Thus, there has been a problem such that the remote radiographing for taking a radiograph for the chest or the like can not be carried out by using the secondary X-ray tube device 1a.

Therefore, there has been a problem such that in case the remote radiographing is carried out, the radiographing must be made by using the secondary X-ray tube device 1a separately installed to the overhead traveling portion 7, and another device where the radiographing device 11 is attached to the Lieder's radiographic stand 22, and FID is set to about 2.0 to 3.0 m.

In the under-tube type fluoroscopic radiographing stand, also, the X-ray tube device 8 and the image receiving system 9 are evacuated toward the head or feet portion of the subject, and the secondary X-ray tube device 1a separately attached to the overhead traveling portion 7 is used in combination with another radiographing device 11 provided under the top board 4 to carry out the remote radiographing for the chest or the like. Therefore, there have been problems such that the device becomes heavy and its operating space becomes narrower.

As described above, in case the remote radiographing is carried out, in addition to the X-ray tube device 8 and the image receiving system 9 attached to the fluoroscopic radiographing stand main portion, the secondary X-ray tube device 1a, the Lieder's radiographic device and another radiographing device 11 are required. Also, in order to detect an X-ray image passing through the subject, the image receiving system 9 and the radiographing device 11 are required.

In view of the above defects, the present invention has been made and an object of the present invention is to provide a radiographic apparatus, wherein the remote radiographing, such as radiographing for the chest or the like, can be carried out by using the radiographic stand capable of fluoroscopic radiographing as the conventional apparatus without separately providing the radiographing device.

Further objects and advantages of the invention will be apparent from the following description of the invention.

SUMMARY OF THE INVENTION

In order to attain the above objects, a radiographic apparatus basically includes a pole for holding an X-ray tube device and an X-ray image detecting portion facing the X-ray tube device to sandwich a top board therebetween so that fluoroscopying or radiographing can be carried out. The radiographic apparatus of the present invention includes an evacuating device operated by a switch for independently evacuating the X-ray tube device together with the pole toward a head or feet side, and a moving device operated by a switch for independently moving the X-ray image detecting portion to a suitable position in an axial direction of a subject's body to thereby carry out fluoroscopying or radiographing in combination with a separately installed secondary X-ray tube device and the X-ray image detecting portion.

Also, in a radiographic apparatus having a pole for holding an X-ray tube device, and an X-ray image detecting portion facing the X-ray tube device to sandwich a top board therebetween so that fluoroscopying or radiographing can be carried out, the radiographic apparatus of the present invention includes a coupling device for mechanically coupling the pole and the X-ray image detecting portion, and a switch for releasing the coupling provided to the radiographic apparatus or its console table. The X-ray image detecting portion, the coupling of which is released by operating the switch, is manually moved in an axial direction of a subject's body.

The radiographic apparatus according to the present invention is structured as described above, so that the X-ray tube device together with the pole can be independently evacuated toward a head or feet side of the subject or patient, and the X-ray image detecting portion can be independently moved to a suitable position in an axial direction of the subject's body. Therefore, in case a remote radiographing suppressing a magnification ratio, such as radiographing for a chest, is carried out, the fluoroscopic radiographing can be carried out in combination with a separately installed secondary X-ray tube device suspended from a ceiling and the X-ray image detecting portion.

Also, a coupling device for the pole and the X-ray image detecting portion is provided, and an interlocking mechanism of the pole and the X-ray image detecting portion is released by a coupling device switch. Thus, only the X-ray tube device can be evacuated by the switch, and the X-ray image detecting portion is manually moved to combine with the secondary X-ray tube device and carry out a remote radiographing.

Also, since only one X-ray image detecting portion is required, an equipment of the present invention can be simplified when compared with the conventional one.

DETAILED DESCRIPTION OF PREFERRED EMBODIMENTS

Figure 1:
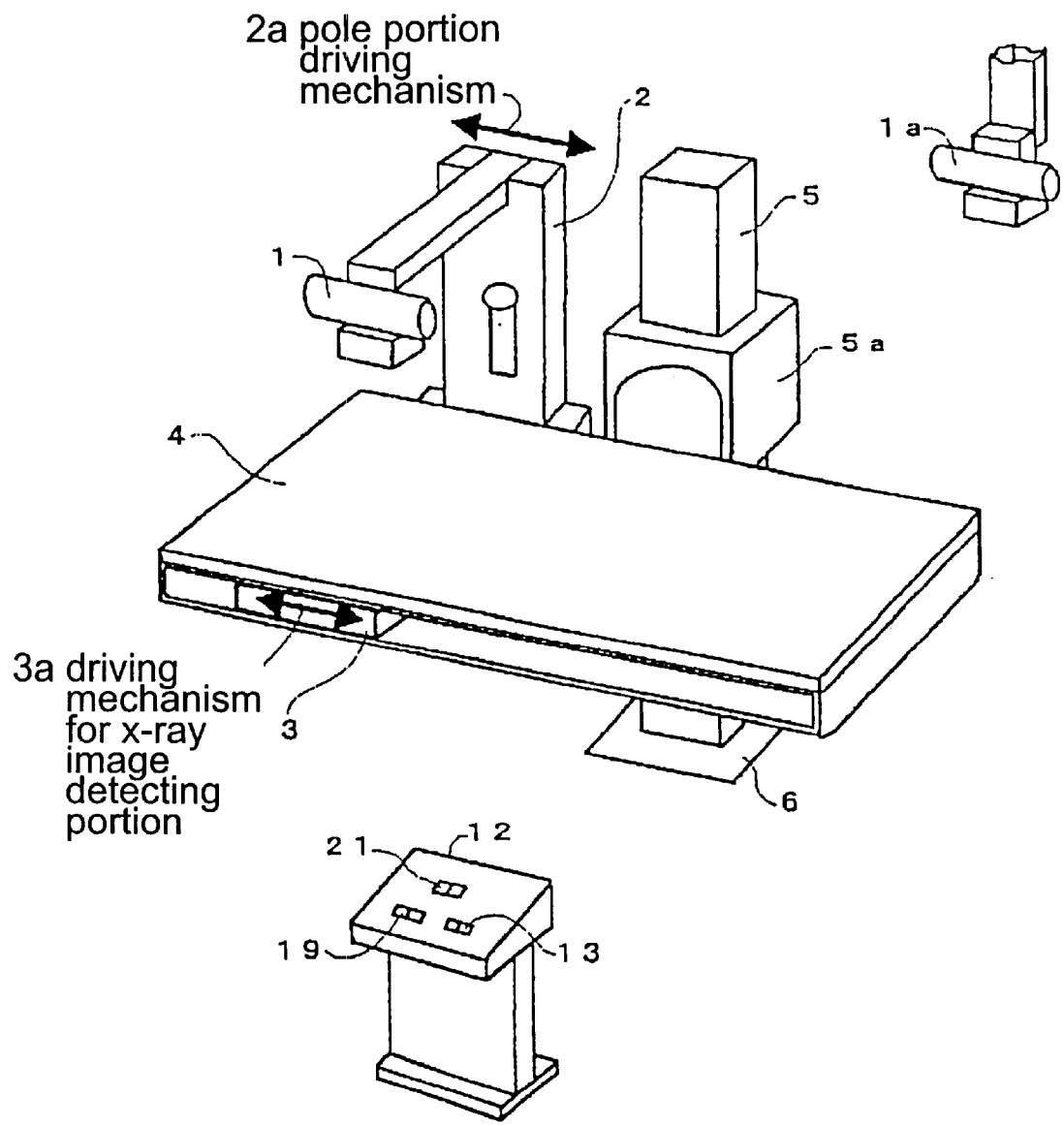
FIG. 1 is a perspective view showing an embodiment of a radiographic apparatus according to the invention.

An embodiment of a radiographic apparatus of the invention is explained with reference to FIG. 1. FIG. 1 is a perspective view showing a radiographic stand, a console table 12 thereof and a secondary X-ray tube device 1a suspended from an overhead traveling portion of the radiographic apparatus of the present invention.

The radiographic apparatus includes an X-ray tube device 1 fixedly supported by a pole 2; a pole-portion driving mechanism 2a for moving the pole 2 parallel to a top board 4; the top board 4 for receiving a subject or patient thereon held by a holding portion 5a of a main pole 5 of a base 6; an X-ray image detecting portion 3 provided under the top board 4; a moving mechanism 3a for the X-ray image detecting portion for moving the X-ray image detecting portion 3 parallel to the top board 4; an evacuating switch 13 for the X-ray tube pole provided on the console table 12 for independently evacuating the pole 2 holding the X-ray tube device 1 parallel to the top board 4 in its longitudinal direction; a moving switch 19 for the X-ray image detecting portion provided on the console table 12 for independently moving the X-ray image detecting portion 3 under the top board 4 parallel to the same in its longitudinal direction; an interlocking switch 21 for driving the X-ray tube device 1 and the X-ray image detecting portion 3 in an interlocked state; and a secondary X-ray tube device 1a suspended from an overhead traveling portion.

In the radiographic apparatus of the invention, when fluoroscopying or radiographing is carried out by using a normal X-ray tube device 1, commands are sent to the respective drive controlling portions from CPU to move in a direction of head to foot of the subject or patient while keeping such a relationship that the X-ray tube device 1 faces the X-ray image detecting portion 3 through the operation of the interlocking switch 21.

When a remote radiographing for suppressing a magnification ratio, such as chest radiographing, is carried out, the pole 2 is evacuated to a head side or foot side of the subject by the evacuating switch 13 for the X-ray tube pole provided at the console table 12 or a radiographic stand main portion. Then, the separately provided secondary X-ray tube device 1a suspended from a ceiling is transferred to a position over the top board 4 where the fluoroscopying or radiographing is carried out, and the X-ray image taking portion 3 is moved to a position facing the X-ray tube device 1a where the fluoroscopying or radiographing is carried out through the operation of the moving switch 19 of the X-ray image detecting portion provided at the console table 12 or radiographic stand main portion. Then, with a combination of the secondary X-ray tube device 1a and the X-ray image detecting portion 3, the fluoroscopying or the radiographing is carried out.

While the interlocking switch 21 interlocks the X-ray tube device 1 and the X-ray image detecting portion 3 through the CPU, the evacuating switch 13 for the X-ray tube pole and the moving switch 19 for the X-ray image detecting portion independently operate the pole 2 or the X-ray image detecting portion 3 through the CPU.

Figure 2:
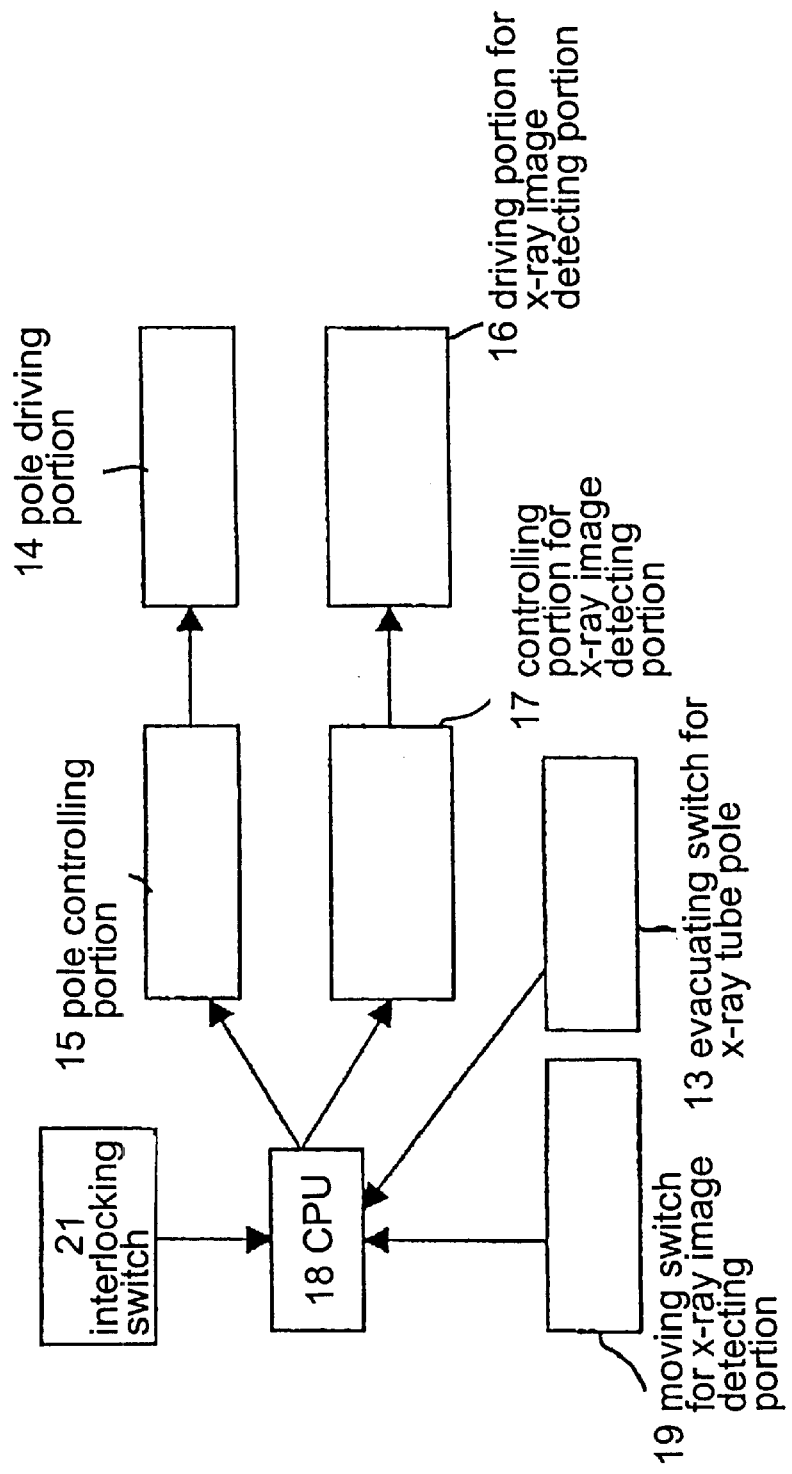
FIG. 2 is a diagram showing a control block circuit of the radiographic apparatus according to the invention.

FIG. 2 shows a block circuit diagram for operating the X-ray tube device 1 and the X-ray image detecting portion 3. The pole portion driving mechanism 2a is formed of the evacuating switch 13 for the X-ray tube pole, CPU 18, pole controlling portion 15 and pole driving portion 14. Also, the driving mechanism 3a for the X-ray image detecting portion is formed of the moving switch 19 for the X-ray image detecting portion, CPU 18, controlling portion 17 for the X-ray image detecting portion, and driving portion 16 for the X-ray image detecting portion. The pole portion driving mechanism 2a and the driving mechanism 3a for the X-ray image detecting portion are controlled by the CPU 18 and operated in an interlocked state through the operation of the interlocking switch 21. However, when the evacuating switch 13 for the X-ray tube pole or the moving switch 19 for the X-ray image detecting portion is operated, they are independently driven.

The X-ray image detecting portion 3 includes a sensor for forming an X-ray image in receipt of X-rays passing through the subject, i.e. an image taking device formed of an image intensifier and semiconductor flat panel. As the image taking device of the semiconductor flat panel, there are two types. One type is formed of X-ray converting membranes for normally converting X-rays into light, photo-diode arrays arranged in a matrix state right under the membranes, and switching elements connected to the respective photo-diode arrays, wherein after irradiation of X-rays, when the respective switching elements are sequentially turned on, signal charges accumulated in the respective pixels are read out to thereby form an X-ray image. The other type is formed of radiation sensor arrays having converting membranes for directly outputting charge signals sensitive to the radiations and corresponding to an amount of incidence, and switching elements connected to electrodes disposed in a matrix state right under the radiation sensor arrays and connected to the electrodes. When X-rays are irradiated, the respective switching elements are sequentially turned on, so that the signal charges accumulated in the respective pixels are read out to thereby form an X-ray image.

In either type of the image taking devices, there are an image taking device where a data storing device is built in to form an image in an off line state; and an image taking device where a signal is sent through on-line from the X-ray image detecting portion 3 of the radiographic apparatus. When the semiconductor flat panel is used, the radiographic apparatus can be made compact since a large space like the image intensifier is not occupied.

Next, operations of the radiographic apparatus are explained. When normal fluoroscopying or radiographing is carried out, first, the subject is laid on the top board 4. Then, an interlocking switch 21 is operated to control the pole controlling portion 15 and the control portion 17 for the X-ray image detecting portion through the CPU 18, so that the pole 2 is moved through the pole driving portion 14, and at the same time, the X-ray image detecting portion 3 is moved by the driving portion 16 for the X-ray image detecting portion. Thereafter, an irradiation lamp of a collimator attached to the X-ray tube device 1 is lighted and a radiation field light is pointed to a concerned portion of the subject so as to align therewith. Then, the fluoroscopying or radiographing is carried out.

When a remote radiographing, such as chest radiographing, by suppressing its magnification ratio, is carried out, first, the evacuating switch 13 for the X-ray tube pole is operated to control the pole controlling portion 15 through the CPU 18, the pole 2 is moved by the pole driving portion 14, and the X-ray tube device 1 is evacuated in either direction along a longitudinal direction of the top board 4. Then, the subject is laid on the top board 4. Next, the secondary X-ray tube device 1a attached to the overhead traveling portion is moved, and the irradiation field light from the collimator is pointed to align with the concerned portion of the subject. Then, the moving switch 19 for the X-ray image detecting portion is operated to control the controlling portion 17 for the X-ray image detecting portion through the CPU 18, and the X-ray image detecting portion 3 is moved to the position where the radiation field light is pointed. Then, the remote fluoroscopying or radiographing is carried out.

Figure 3:
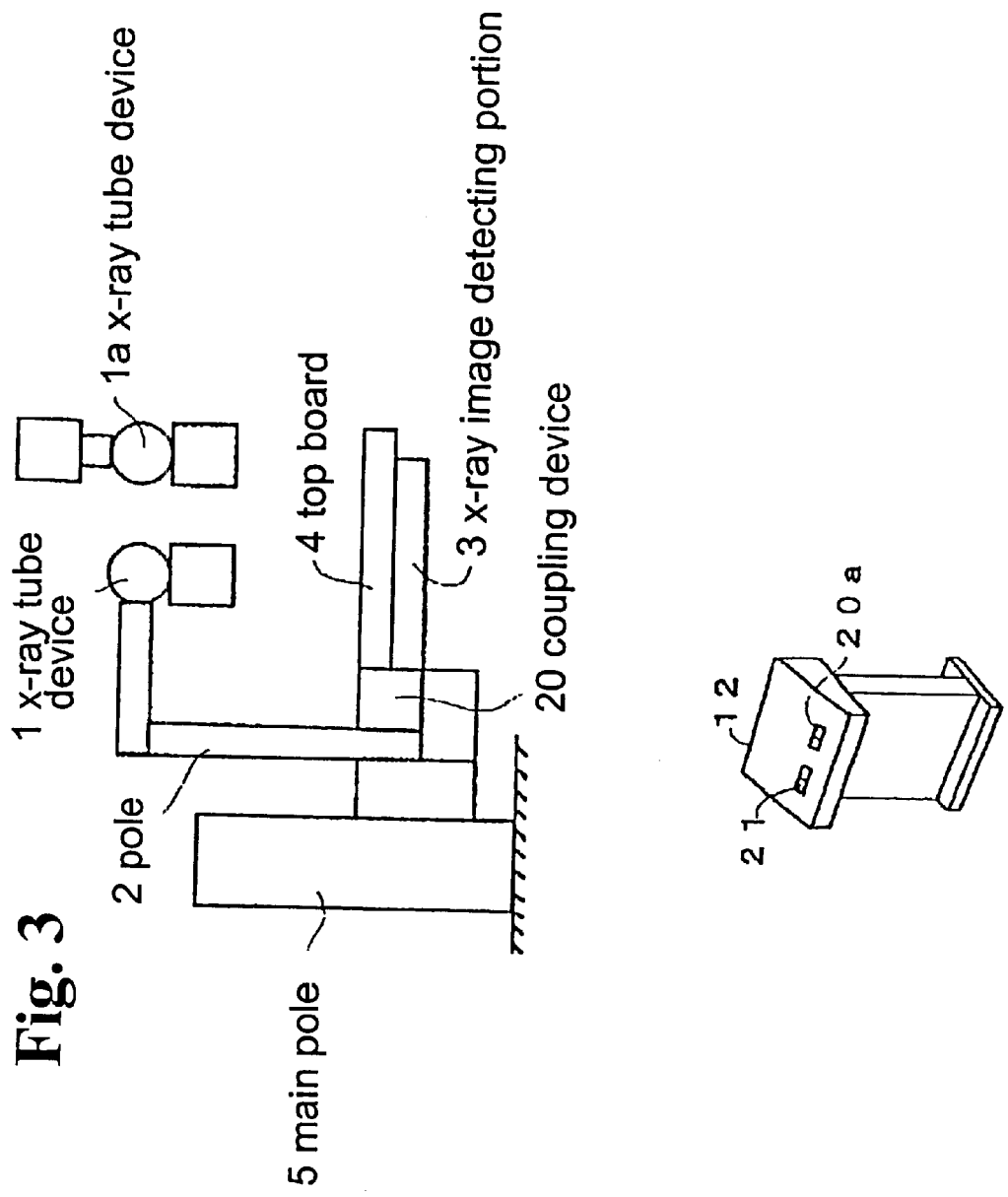
FIG. 3 is a diagram showing another embodiment of the radiographic apparatus according to the invention.
Figure 4:
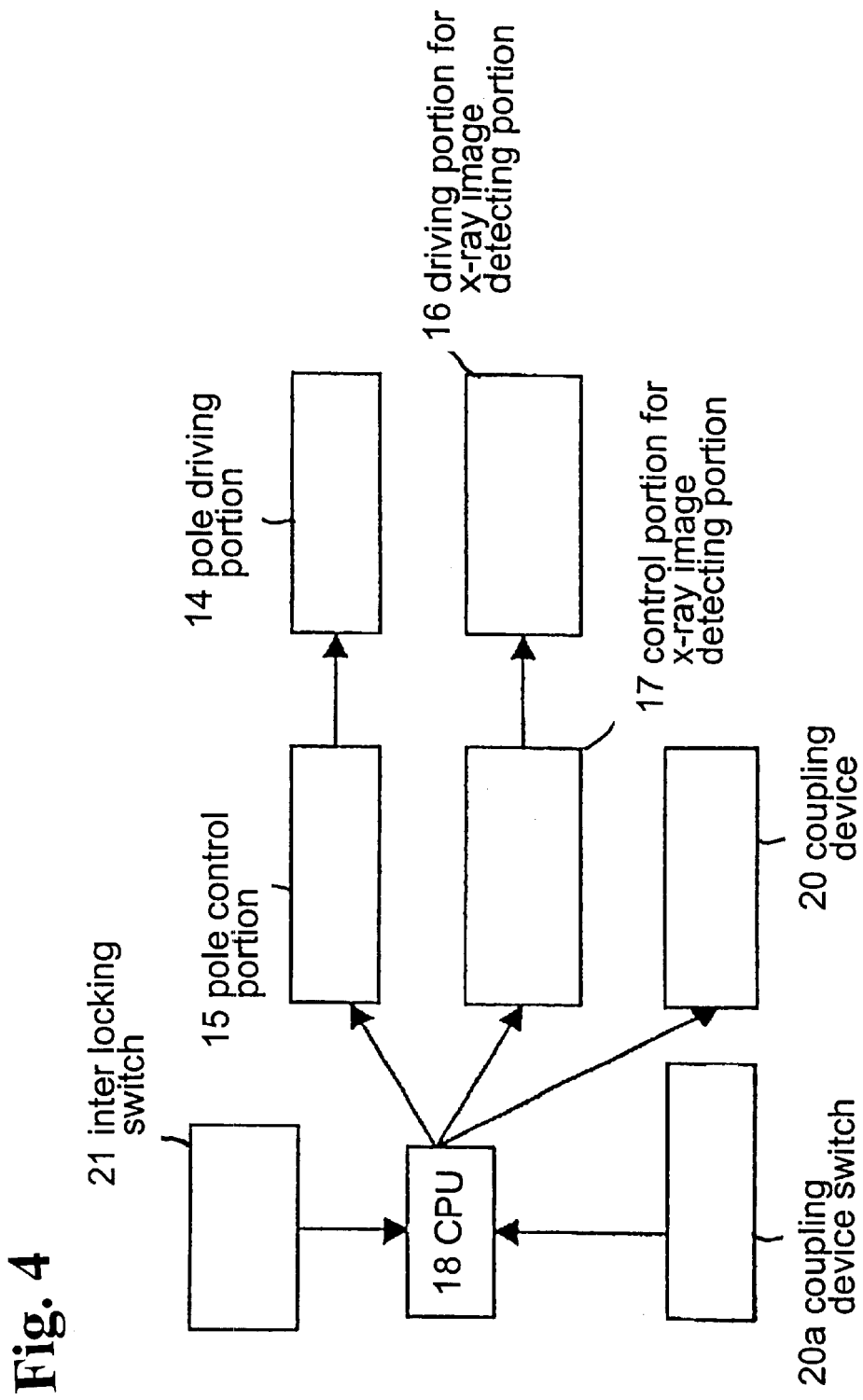
FIG. 4 is a diagram showing another control block circuit of the radiographic apparatus according to the invention.

Another embodiment of the radiographic apparatus is explained with reference to FIGS. 3 and 4. FIG. 3 is a diagram showing a radiographic stand of a radiographic apparatus of the invention, its console table 12, and a secondary X-ray tube device 1a suspended from an overhead traveling portion. FIG. 4 is a block circuit diagram for operating an X-ray tube device 1, an X-ray image detecting portion 3 and a coupling device 20. In the radiographic apparatus, a pole 2 for supporting the X-ray tube device 1 and the X-ray image detecting portion 3 provided under a top board 4 are coupled to face each other by a coupling device 20. When fluoroscopying or radiographing is carried out by the X-ray tube device 1, the pole 2 and the X-ray image detecting portion 3 provided under the top board 4 are used in a coupled state, and the X-ray tube device 1 is used in combination with the X-ray image detecting portion 3 by controlling the pole 2 through the operation of an interlocking switch 21.

In case the fluoroscopying or radiographing is carried out by using the overhead suspension type X-ray tube device 1a, the coupling device 20 is unlocked through the operation of the coupling device switch 20a provided at the console table 12 or radiographic stand main portion to separate the X-ray image detecting portion 3, and the X-ray tube device 1 is evacuated to either direction along the longitudinal direction of the top board 4 by moving only the pole 2 through the operation of the coupling switch 21. Then, the X-ray image detecting portion 3 is positioned by manually operating the same along a rail provided under the top board 4.

Also, coupling by the coupling device 20 may be carried out electrically through the control of the CPU 18 or may be mechanically controlled by a mechanism attached to the radiographic stand main portion. Either way is used.

Figure 5:
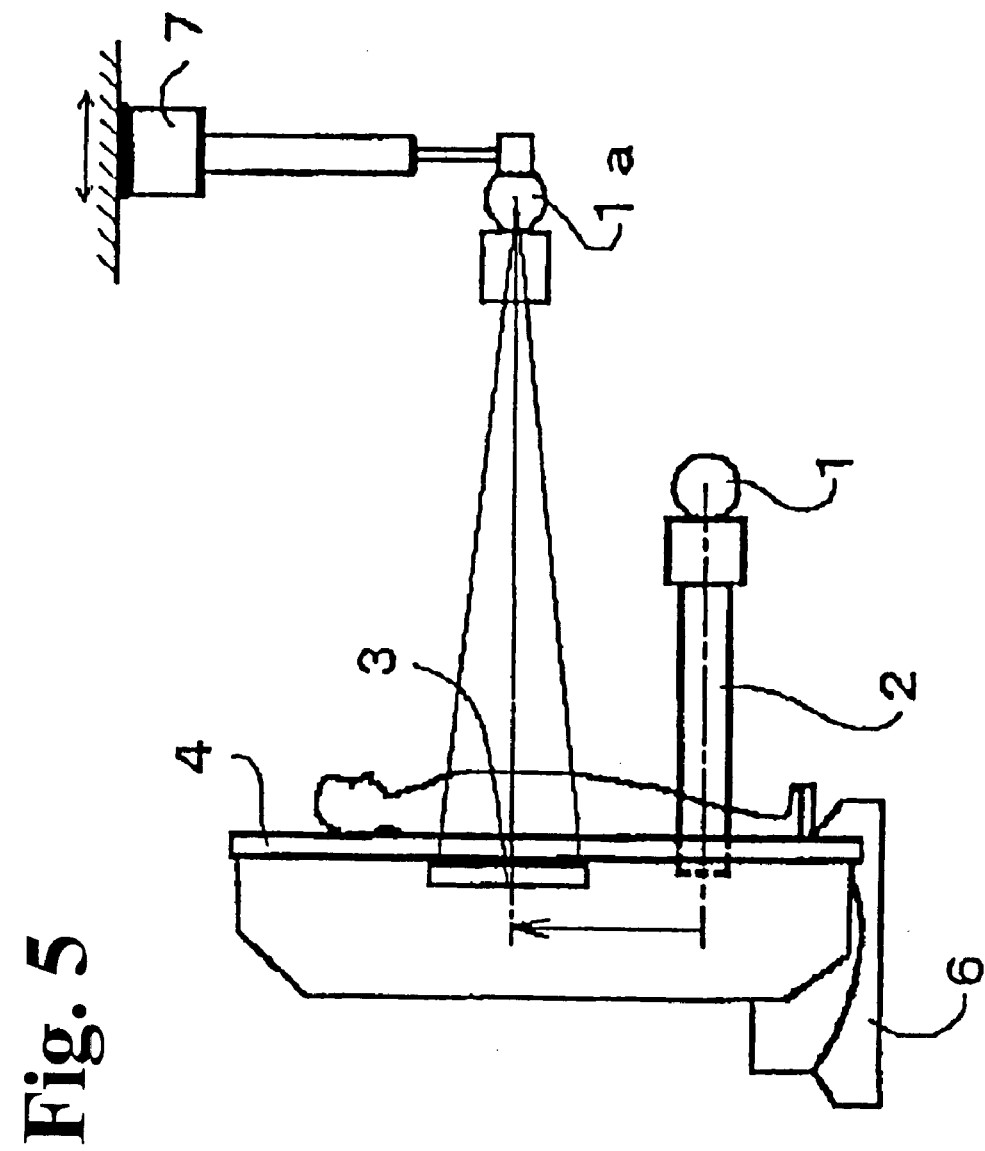
FIG. 5 is a diagram showing a fluoroscopic radiographing stand in an upright position of the radiographic apparatus according to the invention.
Figure 6:
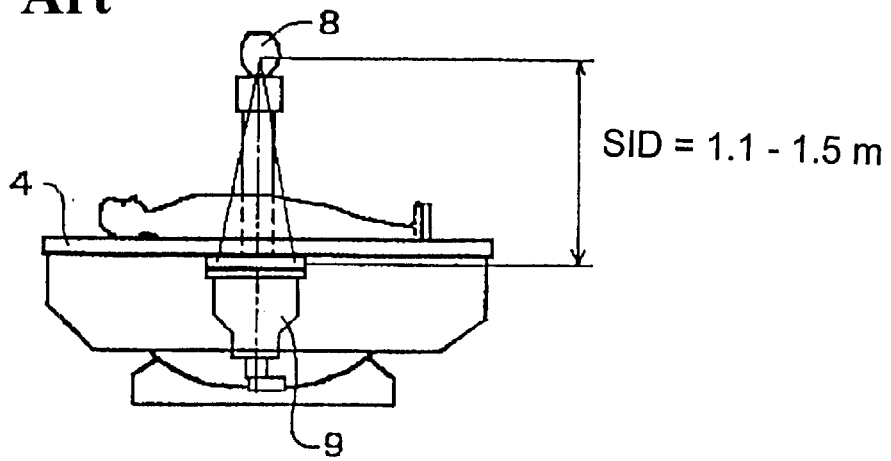
FIG. 6 is a diagram showing a conventional over-tube type fluoroscopic radiographing stand.
Figure 7:
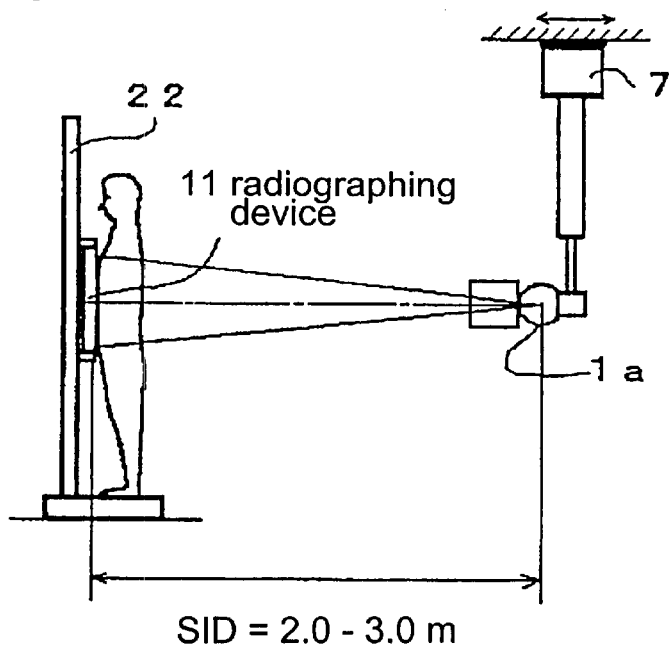
FIG. 7 is a diagram showing a state where a remote radiographing is carried out by using a conventional Lieder's radiographic stand.
Figure 8:
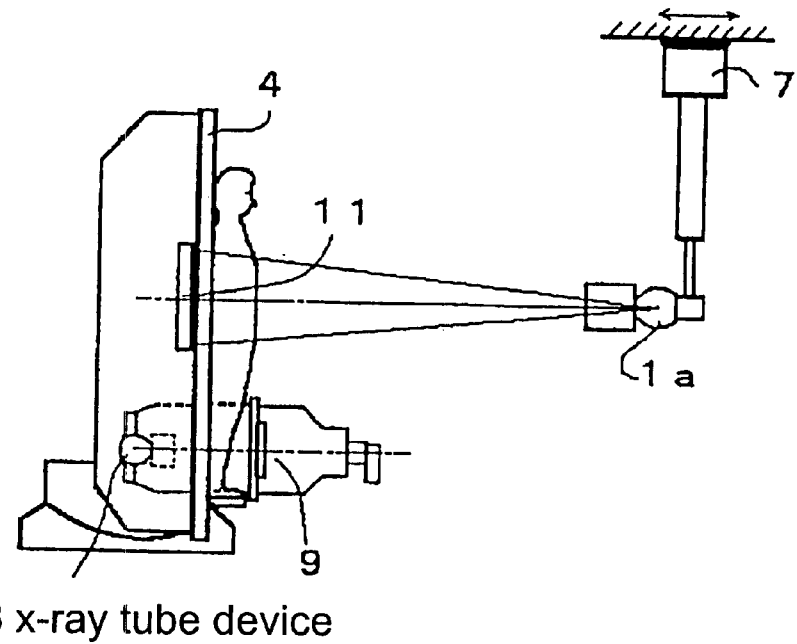
FIG. 8 is a diagram showing a state where a remote radiographing is carried out by using a secondary X-ray tube device with a conventional under-tube type fluoroscopic radiographing stand.
Figure 9:
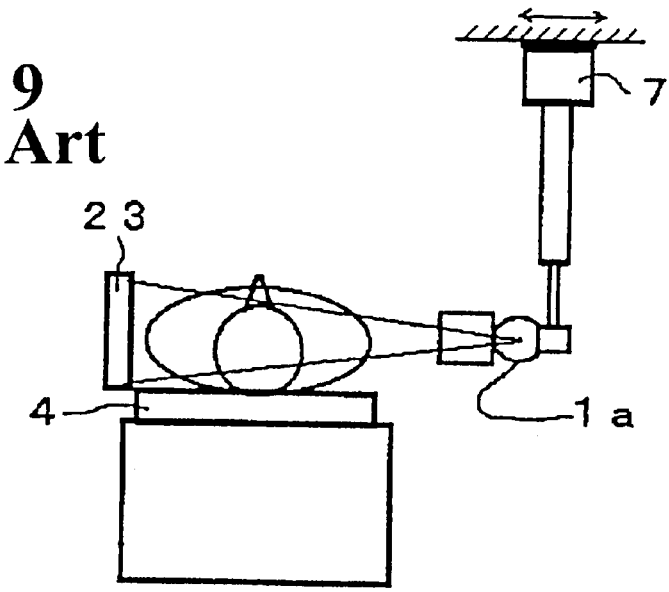
FIG. 9 is a diagram showing a state where a side radiographing is carried out by using the conventional secondary X-ray tube device.

As explained in the above embodiment, only the X-ray image detecting portion 3 is independently moved by releasing the coupling of the X-ray image detecting portion 3 and the pole 2 for supporting the X-ray tube device 1, and then the X-ray image detecting portion 3 is used in combination with the secondary X-ray tube device 1a to thereby carry out remote radiographing, as shown in FIG. 5. Thus, an image taking system can be formed of only one X-ray image detecting portion 3.

Since the radiographic apparatus of the invention is structured as described above, the X-ray tube device can be independently evacuated together with the pole toward the head side or foot side of the subject by operating the pole evacuating switch and the moving switch for the detecting portion disposed on the console table or radiographic stand main portion, or the X-ray image detecting portion can independently be moved to a suitable position in an axial direction of the subject. Therefore, in combination with the separately provided overhead suspension type secondary X-ray tube device and the X-ray image detecting portion, the remote radiographing for suppressing the magnification ratio, such as chest radiographing, can be carried out.

Also, with the coupling device for coupling the pole and the X-ray image detecting portion, the coupling mechanism can be released through the switch. Thus, only the X-ray tube device of the main portion can be evacuated, and the X-ray image detecting portion is moved by the manual operation. Accordingly, the X-ray image detecting portion is combined with the overhead suspension type X-ray tube device to thereby carry out the remote radiographing.

The X-ray image detecting portion of the main portion is used for normal fluoscopying and radiographing. Also, in case of the remote radiographing, the same X-ray image detecting portion can be used in combination with the secondary X-ray tube device. Therefore, the equipment can be simplified when compared with the conventional mechanism. Moreover, when the semiconductor flat panel is used, since it is not required to use a large space for the image intensifier, the radiographic apparatus is made compact, and moreover, the fluoroscopying can be used for positioning.

While the invention has been explained with reference to the specific embodiments of the invention, the explanation is illustrative and the invention is limited only by the appended claims.

What is claimed is:

1. An A radiographic apparatus for fluoroscopy or radiography, comprising:

an X-ray tube device, a pole attached to the X-ray tube device for holding the same, a secondary X-ray tube device, one X-ray image detecting portion disposed to face one of the X-ray tube device and the secondary X-ray tube device, an evacuating device with a switch for independently evacuating the X-ray tube device together with the pole relative to a subject, and a moving device with a switch for independently moving the X-ray image detecting portion to a suitable position so that one of fluoroscopying and radiographing can be carried out by using the X-ray image detecting portion in combination with one of the X-ray tube and the secondary X-ray tube device.

2. A radiographic apparatus according to claim 1, further comprising a top board interposed between the X-ray tube device and the X-ray image detecting portion for allowing the subject to be placed, said evacuating device moving the X-ray tube device and the pole to one of head and foot sides of the subject.

3. A radiographic apparatus according to claim 2, wherein said evacuating device includes a pole portion driving mechanism attached to the pole so that when the switch for the evacuating device is actuated, the pole with the X-ray tube device is moved away from the subject on the top board.

4. A radiographic apparatus according to claim 3, wherein said moving device includes a moving mechanism for the X-ray image detecting portion attached to the X-ray image detecting portion so that when the switch for the moving device is actuated, the X-ray image detecting portion is moved.

5. A radiographic apparatus for fluoroscopy or radiography, comprising:

an X-ray tube device, a pole attached to the X-ray tube device for holding the same, an X-ray image detecting portion disposed to face the X-ray tube device, a coupling device for mechanically coupling the pole and the X-ray image detecting portion, and a switch for actuating the coupling device, said X-ray image detecting portion being released from the pole by an operation of the switch for the coupling device so that the X-ray image detecting portion can be moved manually.

6. A radiographic apparatus according to claim 5, wherein said switch is disposed to one of the radiographic apparatus and an operation table thereof.

7. A radiographic apparatus according to claim 5, further comprising a top board interposed between the X-ray tube device and the X-ray image detecting portion for allowing a subject to be placed, said X-ray image detecting portion being moved along a longitudinal direction of the top board.

* * * * *